United States Patent
Witte et al.

(10) Patent No.: US 10,232,354 B2
(45) Date of Patent: *Mar. 19, 2019

(54) ENHANCED DISPERSION OF EDGE-COATED PRECIOUS METAL CATALYSTS

(71) Applicant: BASF Corporation, Florham Park, NJ (US)

(72) Inventors: Peter Witte, Utrecht (NL); Erica Nollen, Dordrecht (NL); Robert Terorde, Maarn (NL); Lei Zhang, De Meern (NL)

(73) Assignee: BASF Corporation, Florham Park, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/559,837

(22) PCT Filed: Mar. 18, 2016

(86) PCT No.: PCT/IB2016/051546
§ 371 (c)(1),
(2) Date: Sep. 20, 2017

(87) PCT Pub. No.: WO2016/151453
PCT Pub. Date: Sep. 29, 2016

(65) Prior Publication Data
US 2018/0071720 A1    Mar. 15, 2018

(30) Foreign Application Priority Data

Mar. 20, 2015  (NL) ...................... 2014492
Dec. 22, 2015  (NL) ...................... 2016002

(51) Int. Cl.
| | | |
|---|---|---|
| *B01J 23/00* | (2006.01) | |
| *B01J 35/00* | (2006.01) | |
| *C07C 29/00* | (2006.01) | |
| *B01J 23/52* | (2006.01) | |
| *B01J 37/03* | (2006.01) | |
| *B01J 37/16* | (2006.01) | |
| *B01J 37/02* | (2006.01) | |
| *B01J 23/44* | (2006.01) | |
| *C07C 29/17* | (2006.01) | |
| *B01J 21/08* | (2006.01) | |
| *B01J 21/18* | (2006.01) | |
| *B01J 21/06* | (2006.01) | |

(52) U.S. Cl.
CPC ............ *B01J 23/52* (2013.01); *B01J 21/063* (2013.01); *B01J 21/08* (2013.01); *B01J 21/18* (2013.01); *B01J 23/44* (2013.01); *B01J 35/002* (2013.01); *B01J 35/0006* (2013.01); *B01J 35/006* (2013.01); *B01J 35/008* (2013.01); *B01J 35/0013* (2013.01); *B01J 35/0066* (2013.01); *B01J 37/0203* (2013.01); *B01J 37/0211* (2013.01); *B01J 37/0219* (2013.01); *B01J 37/0221* (2013.01); *B01J 37/031* (2013.01); *B01J 37/035* (2013.01); *B01J 37/038* (2013.01); *B01J 37/16* (2013.01); *C07C 29/17* (2013.01)

(58) Field of Classification Search
CPC ............ B01J 23/44; B01J 23/52; B01J 35/00
See application file for complete search history.

(56) References Cited

U.S. PATENT DOCUMENTS

| 4,212,824 | A | 7/1980 | Seagraves |
| 4,361,500 | A | 11/1982 | Máthe et al. |
| 6,090,746 | A | 7/2000 | Bönnemann et al. |
| 2009/0047559 | A1 | 2/2009 | Terada et al. |
| 2011/0015451 | A1 | 1/2011 | Witte |
| 2011/0123909 | A1 | 5/2011 | Mizutani et al. |

FOREIGN PATENT DOCUMENTS

WO   2009/096783 A1   8/2009

OTHER PUBLICATIONS

U.S. Appl. No. 15/559,458, filed Sep. 19, 2017, Peter Witte, et al.
International Search Report and Written Opinion of the International Searching Authority dated Jul. 15, 2016 in PCT/IB2016/051546 filed Mar. 18, 2016.
International Preliminary Report on Patentability dated Jun. 2, 2017 in PCT/IB2016/051546 filed Mar. 18, 2016.
T. Teranishi, et al., "Size Control of Palladium Nanoparticles and Their Crystal Structures" Chemistry of Mater., vol. 10, No. 2, 1998, pp. 594-600.
John Turkevich, et al., "Palladium: Preparation and Catalytic Properties of Particles of Uniform Size" Science, vol. 169, Issue 3948, Aug. 28, 1970, pp. 873-879 and Cover page.
A. C. Vermeulen, et al., "Hydrolysis-Precipitation Studies of Aluminum (III) Solutions I. Titration of Acidified Aluminum Nitrate Solutions" Journal of Colloid and Interface Science, vol. 51, No. 3, Jun. 1975, pp. 449-458.
Peter T. Witte, et al., "NanoSelect Pd Catalysts: What Causes the High Selectivity of These Supported Colloidal Catalysts in Alkyne Semi-Hydrogenation?" ChemCatChem, vol. 5, Issue 2, Nov. 9, 2012, pp. 582-587.
International Search Report dated Jul. 15, 2016 in PCT/IB2016/051546 filed Mar. 18, 2016.

*Primary Examiner* — Sikarl A Witherspoon
(74) *Attorney, Agent, or Firm* — Oblon, McClelland, Maier & Neustadt, L.L.P.

(57) ABSTRACT

The present invention is in the field of catalysis. More particularly, the present invention is directed to supported precious metal, preferably palladium and/or gold metal catalysts, having a high degree of dispersion and a high degree of edge-coating. The present invention is further directed to a process for producing these catalysts, as well as to the use of these catalysts in chemical reactions.

18 Claims, 4 Drawing Sheets

ENHANCED DISPERSION OF EDGE-COATED PRECIOUS METAL CATALYSTS

CROSS-REFERENCE TO RELATED APPLICATIONS

This application is a National Stage of PCT/IB2016/051446, which was filed on Mar. 18, 2016. This application is based upon and claims the benefit of priority to Netherlands Application No. 2014492, which was file don Mar. 20, 2015, and to Netherlands Application No. 2016002, which was filed on Dec. 22, 2015.

BACKGROUND OF THE INVENTION

The present invention is in the field of catalysis. More particularly, the present invention is directed to supported precious metal catalysts, preferably palladium and/or gold metal catalysts, having a high degree of dispersion and a high degree of edge-coating. The present invention is further directed to a process for producing these catalysts, as well as to the use of these catalysts in chemical reactions.

Many supported precious metal (PM) catalysts are used inter alia for selective conversion of fine chemicals, which are typically highly functionalized large molecules. In order for the PM crystallites to be best accessible for the large molecules, it is desirable to have them situated in the outer shell of the support as much as possible. This is referred to as an edge-coated metal distribution. Typically a high degree of edge-coating is achieved when the majority of the PM crystallites are situated in the outer shell of the support. Such an edge-coated distribution has the additional advantage that the substrate molecule rapidly leaves the vicinity of the PM crystallite after it is converted, thereby minimizing any side reactions from taking place. However, the preparation of edge-coated catalysts with a high dispersion is difficult. Since only a small portion of the total surface area of the support is used, edge-coated catalysts generally have a low dispersion.

Supported precious metal catalysts are typically prepared by a deposition-reduction method, in which the metal is first deposited on a support and then reduced. In order to prepare a catalyst with a high dispersion, typically a deposition-precipitation preparation procedure is carried out in which the metal salt has time to diffuse into the pores of the support. In this way, a high dispersion is achieved by the metal being distributed over the complete surface area of the support. This provides a large active metal surface area since the formed metal crystallites are very small, typically in the order of a few nanometers. On the other hand, for the preparation of edge-coated catalysts, the metal salt should not diffuse too deep into the pores of the support (i.e. typically less than 100 nm into the pores for a support particle having an average size of about 20 to 100 micron), but should deposit immediately upon contact with the support. These two methods contradict each other, so the preparation of high-dispersed edge-coated metal catalysts is typically a compromise between these two factors.

Heterogeneous catalysts based on colloidal suspensions are characterized by small metal crystallite sizes, see for instance P. T. Witte, S. Boland, F. Kirby, R. van Maanen, B. F. Bleeker, D. A. M. de Winter, J. A. Post, J. W. Geus, P. H. Berben, *Chem Cat Chem.* 5 (2013) 582-587. The present invention aims at producing catalysts having even smaller precious metal particle (crystallite) sizes, in particular nanop articles that are about the same size and/or smaller than the average pore size of the support. Furthermore, the present invention aims at producing catalysts wherein the supports are edge coated with the PM crystallites.

Also WO-A-2009/096783 describes the preparation of an aqueous colloidal precious metal suspension, which process comprises reducing a precious metal salt in aqueous solution using a functionalized, water soluble quaternary ammonium salt in the absence of organic solvents, to form elementary nanoparticles. Although this known method yields small precious metal particles, there is still a need for catalysts having even smaller precious metal crystallites, which are distributed as described above.

In U.S. Pat. No. 4,212,824 a platinum on a carbon black support catalyst is described with an improved metal distribution as determined by ESCA (electron spectroscopy for chemical analysis), but in this document the metal dispersion is not specified. Also, the carbon black support used in this document has a low surface area (i.e. 20-100 $m^2/g$).

Accordingly it is a first object of the present invention to provide a precious metal catalyst, in particular a palladium or gold metal catalyst, which is not only edge coated but also has a high metal dispersion. Another object of the present invention is to provide a process for producing said catalyst. A further object of the present invention is to provide said catalyst, so that it may be used in chemical reactions.

BRIEF SUMMARY OF THE INVENTION

Surprisingly it has been found that the edge-coating and metal dispersion of the catalyst can be controlled separately. As a result, both parameters can be optimized separately to obtain highly dispersed edge coated precious metal catalysts, in particular palladium and/or gold metal catalysts, according to the present invention, thus meeting at least one of the above-mentioned objects.

The present invention is accordingly directed to a precious metal catalyst, wherein said catalyst comprises nanocrystallites of the precious metal on a powder support, wherein the precious metal is palladium and/or gold metal;

wherein the palladium metal catalyst comprises nanocrystallites having an average size of from 1 to less than 5 nm, and wherein said catalyst has a surface enrichment value of from at least 6.5 to at most 150; and, wherein the gold metal catalyst comprises nanocrystallites having an average size of from 3 to less than 15 nm, and wherein said catalyst has a surface enrichment value of from at least 3 to at most 150.

DETAILED DESCRIPTION

Figure 1:
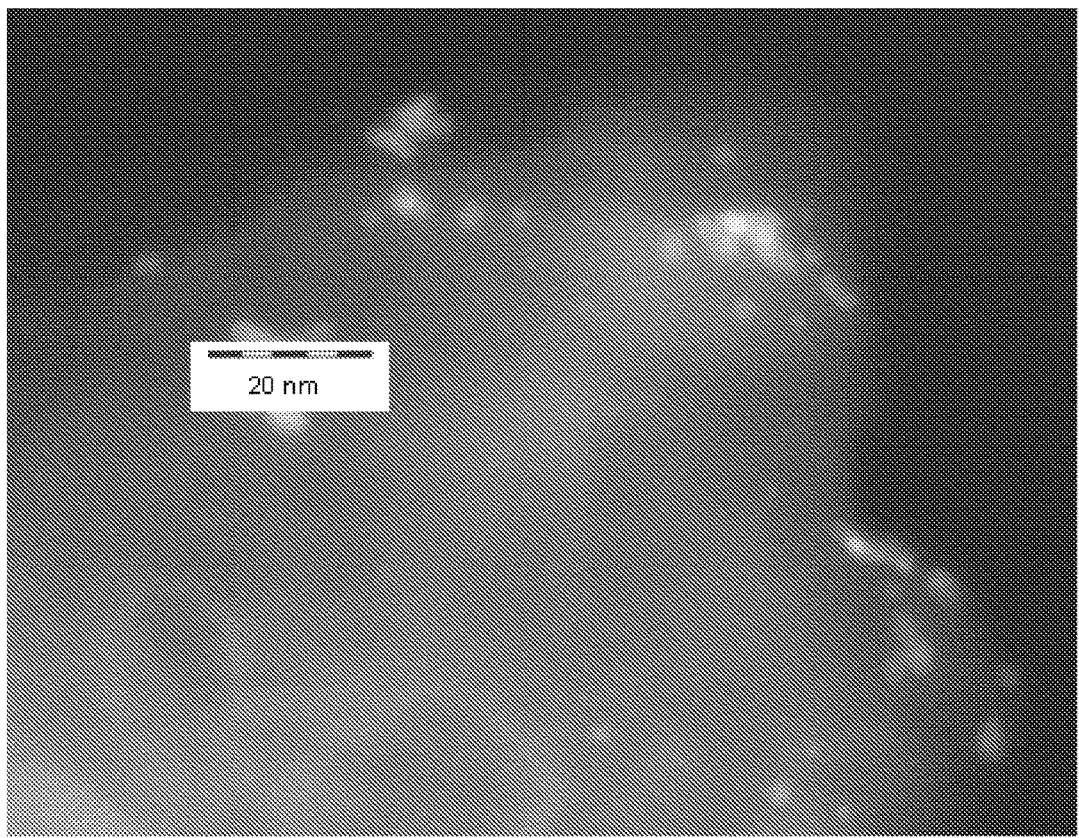
FIGS. 1-6 show TEM images of catalysts of the present disclosure.

Typically, a palladium metal catalyst of the present invention comprises nanocrystallites of palladium metal having an average size of from 1 to less than 5 nm, preferably between 1 and 4 nm and more preferably between 1.5 and 3 nm.

A gold metal catalyst of the present invention typically comprises nanocrystallites of gold metal having an average size of from 3 to less than 15 nm, preferably between 3 and 13 nm and more preferably between 5 and 10 nm.

The average size of the precious metal nanocrystallites, as used herein, is based on the value that can be determined by Transmission Electron Micrograph (TEM), unless otherwise indicated.

Typically, a palladium metal catalyst of the present invention has a surface enrichment value of at least 6.5, preferably at least 8 and more preferably at least 10. The surface enrichment value of the palladium metal catalyst is typically at most 150, preferably at most 120, and more preferably at most 90.

A gold metal catalyst of the present invention typically has a surface enrichment value of at least 3, preferably at least 5 and more preferably at least 7. The surface enrichment value of the gold metal catalyst is typically at most 150, preferably at most 120, and more preferably at most 90.

Surprisingly it has been found that the catalyst of the present invention has a high activity due to a combination of the high metal dispersion, which increases the number of active sites available to the reactants as well as the contribution of atoms at the corners or edges of the metal nanocrystallites, and high edge-coating, which leads to improved accessibility for reactants to the catalytic metal surface. The catalyst of the present invention also surprisingly has the advantage of a high selectivity due to the edge-coating which decreases the likelihood of undesirable side reactions. A further advantage of the catalyst of the present invention is that internal heat transfer problems will not occur when it is used in an exothermic chemical reaction, because the precious metal is present mostly on the surface of the support. Therefore any heat that is generated during the chemical reaction is able to be easily transferred into the surrounding reaction mixture.

The surface enrichment value (SEV) can be determined by using X-ray photoelectron spectroscopy (XPS) and inductively coupled plasma (ICP) measurements, in particular inductively coupled plasma optical emission spectrometry (ICP-OES) measurements, and the following formula (I):

$$SEV = (XPS\ wt.\ \% - ICP\ wt.\ \%) / ICP\ wt.\ \% \quad (I)$$

wherein XPS wt. % is the XPS measurement and ICP wt. % is the ICP measurement (i.e. ICP-OES measurement) of the PM content of the catalyst according to the present invention, in weight percent (wt. %) (. XPS measurements are used to determine the content of the precious metal in the outer shell of the powder support (i.e. typically about 0 to 10 nm in depth from the surface of the powder support particle), in weight percent (wt. %). ICP measurements (i.e. ICP-OES measurements) are used to determine the precious metal content in the powder support (i.e. a bulk measurement), in weight percent (wt. %).

A perfectly uniform distribution of precious metal on the powder support typically has the same precious metal content as determined for both XPS and ICP measurements (i.e. ICP-OES measurements) and would result in a surface enrichment value of zero. In the case of an edge-coated metal distribution, the precious metal content in the outer shell of the catalyst powder support, as determined by XPS measurement, should be considerably higher than that in the powder support, as determined by ICP measurement (i.e. ICP-OES measurement). The reason that XPS measurements only give information on the outer few nanometers (i.e. typically about 5-10 nm in depth from the surface of the measured material) of the measured material, is that although the X rays penetrate deep into a material, the released photoelectrons will only be measured if they have enough energy to escape from the material. The released photoelectrons can undergo inelastic collisions, recombination, excitation of the sample, recapture or trapping in various excited states within the material, all of which can reduce the number of escaping photoelectrons. These effects appear as an exponential attenuation function as the depth increases, making the signals detected from elements at the surface much stronger than the signals detected from elements deeper below the material surface. Therefore, an XPS measurement typically only gives information on the outer few nanometers of the measured material.

Unless explicitly indicated otherwise, all ICP measurements (i.e. ICP-OES measurements) of the catalysts, as used herein, are the values that can be measured on a Thermo Scientific™ iCAP™ 7400 ICP-OES Analyzer having an aerosol concentric nebulizer, using the autosampler CETAC ASX-260 and typically calibration curves of 0-25 ppm. Two standard series typically used were of 0 ppm (blank); 5, 10 and 25 ppm of the elements Pd, Pt, Rh, and Ru, with each element having the same concentration, and with one of the series in an aqueous solution of 10 wt. % nitric acid (concentration of 65 wt. %) and the other series in an aqueous solution of 15 wt. % of $H_3PO_4/H_2SO_4$ (5:3) ($H_3PO_4$ having a concentration of 85 wt. %, and $H_2SO_4$ having a concentration 98 wt. %). Typically all measurement series performed started with the standards, so as to determine the calibration curve and ensure that the correlation coefficient was greater than 0.999. The standard of 10 ppm was usually used as an internal standard during a series measurement All XPS measurements of the catalysts, as used herein, unless explicitly indicated otherwise, are the values that can be measured using a Phi Versa Probe 5000 spectrometer using monochromatic Al Kα radiation (80 W). The instrument work function was calibrated to give a binding energy (BE) of 84.0 eV for the Au 4f7/2 line of metallic gold and the spectrometer dispersion was adjusted to give a BE of 932.6 eV for the Cu 2p3/2 line of metallic copper. The built in Phi charge neutralizer system was used on all samples measured. To minimize the effects of differential charging, all catalyst samples were usually mounted and insulated against the ground. Typically, the catalyst samples were prepared as a thin powder film on double-faced adhesive tape.

XPS survey scan analyses of the catalyst samples were typically carried out with an analysis area of 0.1×1.4 mm, a pass energy of 117 eV and an energy step size of 0.5 eV. High resolution analyses were usually carried out on the same analysis area with a pass energy of 23.5 eV and an energy step size of 0.1 eV. Three XPS measurements were usually made per catalyst sample. Energy correction of the spectra obtained was usually performed in such a manner, that the position of the 1s-signal of C was at a binding energy of 284.5 eV.

Quantification of elemental abundance was usually determined from the XPS survey spectra by employing a Shirley background subtraction and using the transmission function correction and elemental sensitivity factors provided by the manufacturer of the above-mentioned spectrometer. The concentration of an element determined in atomic % was converted into mass (i.e. weight) % using the following formula (II):

$$C(Element)[mass - \%] = \quad (II)$$

$$\frac{C(\text{Element})[\text{at}-\%] \times M(\text{Element})\left[\frac{\text{g}}{\text{mol}}\right]}{\sum_{\text{all elements}} C(\text{Element})[\text{at}-\%] \times M(\text{Element})\left[\frac{\text{g}}{\text{mol}}\right]} \times 100$$

wherein C(Element)[mass-%] is the concentration of the element in mass (i.e. weight %), C(Element)[at-%] is the concentration of an element in atomic %, and M(Element) [g/mol] is the molar mass of an element in g/mol The catalyst of the present invention typically comprises precious metal, in particular palladium and/or gold metal, in an amount of between 0.01 and 20 wt. %, preferably between 0.1 and 15 wt. %, and most preferably between 0.3 and 10 wt. %, based on the weight of the catalyst. All wt. % referred to herein are based on the weight of the isolated and washed and dried catalyst, unless otherwise indicated.

The powder support of the catalyst of the present invention may be selected from the group consisting of silica, alumina, zirconia, titanium oxide, ceria, magnesium oxide, zinc oxide, metal silicates (e.g. titanium silicates (TiS)), metal aluminates, zeolites, carbon nanotubes, carbon nanofibres, graphitic carbon and activated carbon (AC) and combinations thereof, and preferably activated carbon and/or metal silicates, in particular titanium silicates.

The BET surface area of the oxidic supports is typically more than 50 m$^2$/g. Typically the BET surface area of the oxidic supports is less than 1000 m$^2$/g. The BET surface area of carbon based supports, such as activated carbon, typically have a higher BET surface area of more than 400 m$^2$. Typically the BET surface area of the carbon based supports, such as activated carbon, is less than 3000 m$^2$/g. The BET surface area, as used herein, is the value that can be measured by determining the amount of nitrogen adsorbed at 77 K and P/P$_o$ of approximately 0.3 and assuming a nitrogen cross sectional area of 16.2 Å$^2$, after degassing the sample at 180° C. on a Micromeritics ASAP 2420.

Activated carbon is the preferred support to be used in the catalyst of the present invention since it has a high BET surface area, is economically cost effective, and allows easy recovery of the precious metal by simply oxidizing the catalyst at an elevated temperature.

Typically the average particle size of the powder support is between 0.1 and 500 micron. The average particle size (i.e. volume average particle size) of the powder support, as defined herein, is the value as determined from the volume particle size distribution, in particular the volume mean diameter D(v0.9), wherein D(v0.9) is the diameter where 90% of the distribution is above and 90%, as measured by laser diffraction with a Malvern MS 2000 system and sampling unit Hydro 2000G, corresponding to a measuring range of 0.02-2000 μm using the "General purpose" as the model for calculating the average particle size.

The micropore surface area of the powder support is typically between 10 and 1100 m$^2$/g, preferably between 20 and 1000 m$^2$/g, and more preferably between 30 and 800 m$^2$/g. The micropore surface area, as used herein, is the value that can be determined from a t-plot analysis, as described in Applied Catalysis A: General 174 (1998) 137-146 and determined using the suite of software programs on a Micromeritics ASAP 2040 using nitrogen as the adsorbate at the temperature of liquid nitrogen.

Typically, the powder support of the catalyst of the present invention is microporous and/or mesoporous.

In an additional embodiment, the present invention is directed to a process for preparing a precious metal catalyst according to the present invention, wherein said process comprises the steps of:
  reducing a precious metal compound in an aqueous solution by contacting said solution with a reducing agent, a stabilizing agent and a coordinating agent to form a colloidal precious metal suspension;
  contacting the suspension with a powder support; and,
  recovering the precious metal catalyst.

The advantage of the process of the present invention is that the precious metal dispersion is set in the first step. This is done using a colloidal approach, in which the precious metal compound is reduced to precious metal crystallites in an aqueous solution in the presence of a reducing agent, a stabilizing agent and a coordinating agent to form a colloidal suspension. Typically, the precious metal compound in the aqueous solution is contacted, in particular mixed, with the reducing agent, the stabilizing agent and the coordinating agent. In the following step the edge coating is set by depositing the resulting colloidal suspension onto a suitable powder support by contacting the suspension, in particular by mixing, with the support to obtain the catalyst of the present invention.

Preferably the precious metal is palladium and/or gold metal.

Suitable precious metal compounds which may be used include water soluble salts, such as nitrates, acetates, sulfates, ammonium citrates and chlorides and combinations thereof. Preferably, the salt used is Na$_2$PdCl$_4$ and/or AuCl$_3$.

The reducing agent and stabilizing agent, as used in the process of the present invention, may comprise of one compound or more than one compound, which acts as both a reducing agent and a stabilizing agent.

The reducing agent acts in the process of the invention to reduce the precious metal compound in an aqueous solution (i.e. precious metal ions) to precious metal particles.

The stabilizing agents acts in the process of the invention to stabilize the precious metal particles formed by contacting the precious metal compound with the reducing agent in an aqueous solution, thereby forming a colloidal precious metal suspension. The advantage of using a stabilizing agent according to the process of the invention is that it prevents or minimizes precious metal agglomeration and particle growth.

Suitable reducing agents which may be used in the process according to the present invention include a quaternary ammonium salt, sodium formate, formic acid, sodium citrate, citric acid, hydrazine, alcohols (e.g. typically C$_1$-C$_4$ alcohols but also diols or polyols), borohydrides, formaldehyde, hypophosphite, metal alkalydes, hydrogen and combinations thereof.

Preferably, the reducing agent is a quaternary ammonium salt, and more preferably is a functionalized quaternary ammonium salt. In this respect the functionalization comprises the presence of at least one reducing group, selected from the group consisting of primary alcohols, secondary alcohols, cyclohexenyl and combinations thereof, preferably in combination with at least one bulky group selected from the group consisting of C$_{3+}$ alkyls (i.e. C$_4$-C$_{20}$ alkyls), cycloalkyl, aralkyl, alkaryl and aryl groups and combinations thereof, and wherein the at least one bulky group is optionally functionalized with at least one —OH and/or cyclohexynol group. In addition the quaternary ammonium salt can be chiral, such as a quaternized cinchonine or cinchonidine.

Most preferably the quaternary ammonium salt which may be used in the process of the present invention is of the formula (III):

$$RR'R''-N^+-CH_2CH_2OH\ X^- \qquad (III)$$

wherein R, R', and R" are independently of each other $C_1$-alkyl and higher (i.e. $C_4$-$C_{20}$ alkyls), wherein the $C_1$-alkyl and higher (i.e. $C_4$-$C_{20}$ alkyls) are optionally functionalized with at least one —OH and/or cyclohexynol group and X is $Cl^-$, $Br^-$, $H_2PO_4^-$, $NO_3^-$ or $HSO_4^-$. Preferably, R and R' are $C_1$-alkyl, and R" is selected from $C_3$-alkyl and higher (i.e. $C_4$-$C_{20}$ alkyls), more preferably $C_{16}$-alkyl.

Typically, the amount of reducing agent used in the process according to the present invention is at least 3 molar equivalents, and preferably at least 5 molar equivalents, of the amount of the precious metal compound to be reduced. The amount of reducing agent typically used in the process of the present invention is at most 40 molar equivalents, and preferably at most 25 molar equivalents, of the amount of the precious metal to be reduced.

Suitable stabilizing agents which may be used in the process of the present invention include a quaternary ammonium salt, donor ligands (e.g. phosphines, amines and/or thioethers ligands), polymers (e.g. poly(vinylpyrrolidone) (PVP), poly(vinyl alcohol) (PVA), and/or poly(methylvinyl ether)), surfactants and combinations thereof, preferably is a quaternary ammonium salt, and more preferably is a functionalized quaternary ammonium salt, wherein the functionalization is according to that as described herein above.

Typically, the amount of stabilizing agent used in the process according to the present invention is at least 3 molar equivalents, and preferably at least 5 molar equivalents, of the amount of the precious metal compound to be reduced. The amount of stabilizing agent typically used in the process of the present invention is at most 25 molar equivalents, and preferably at most 10 molar equivalents, of the amount of the precious metal compound to be reduced.

The advantage of using a quaternary ammonium salt as a reducing agent is that it also acts as a stabilizing agent which minimizes the number of reagents used in the process according to the present invention. A further advantage is that most of the reducing agents described are volatile or produce volatile products, while a quaternary ammonium salt, which is basically an ionic liquid, has no vapor pressure and can be used in production without the necessary safety requirements that are needed for reducing agents, such as low boiling organic solvents.

The coordinating agent acts in the process of the invention to coordinate to the precious metal compound in an aqueous solution during the reduction. The advantage of using a coordinating agent is that it results in a reduction in the size of the precious metal particles produced (i.e. higher dispersion), in comparison to when no coordinating agent is used.

A coordinating agent which may be used in the process of the present invention is urea and/or ammonia.

The amount of a coordinating agent which may be used in the process of the present invention is typically 0.5 or more molar equivalents of the amount of the precious metal compound to be reduced. The amount of coordinating agent typically used in the process of the present invention is at most 25 molar equivalents, of the amount of the precious metal compound to be reduced. Preferably, the amount of coordinating agent used in the process of the present invention is 0.5-15 molar equivalents of the amount of the precious metal compound to be reduced. Even more preferably, the amount of coordinating agent used in the process of the present invention is 1-15 molar equivalents of the amount of the precious metal compound to be reduced.

Suitable concentrations of the precious metal solutions which may be used in the process of the present invention are preferably 0.1-10 g/L, more preferably 0.1-8 g/L and even more preferably 0.2-5 g/L, wherein the g/L is based on the weight of the PM in the PM compound used.

The use of urea to prepare supported metal catalysts by a so-called homogeneous deposition-precipitation method has been described in literature, see for instance A. C. Vermeulen, J. W. Geus, R. J. Stol and P. L. de Bruyn, *J. Colloid and Interface Science* 51(1975)449). In this method the metal and support are mixed and heated in the presence of urea. This results in the hydrolysis of urea to the basic species of $CO_2$ and $NH_3$ which causes the pH to rise, and the subsequent deposition of the metal species onto the support. Addition of the basic species to the reaction mixture is not performed since it causes an inhomogeneous increase of the pH. The deposited metal species is reduced in a subsequent step.

In the process of the present invention the coordinating agent is not added in the deposition step, but in the reduction step. Surprisingly it has been found that urea and/or ammonia acts as a coordinating agent for the reduction of the precious metal compound, which is indicated by the higher temperature that is required for the metal reduction to take place.

Suitable temperatures for the solutions used in the process of the present invention typically range from between 10 to 95° C. Preferably, the temperature used in the reduction step is 10 to 50° C. when reducing a gold metal compound; or, the temperature used in the reduction step is 50 to 95° C. when reducing a palladium and/or platinum metal compound. The deposition step may preferably be carried out at a temperature of 10 to 50° C.

It has also been reported that an increase in reduction temperature leads to a smaller metal crystallite size of the formed colloids (T. Teranishi, M. Miyake, *Chem. Mater.* 10 (1998) 594). However, it is not possible to simply take a mixture of a metal compound and a stabilizer and heat that mixture to a higher temperature than as described in WO-A-2009/096783, since the reduction will take place during the heating. Further, the addition of a metal compound to a stabilizer at increased temperatures disadvantageously leads to a broad metal crystallite size distribution.

In the literature several reaction parameters, such as metal concentration, pH and the amount of stabilizer, are described which can be used for tuning the size of the obtained metal crystallites, see for example J. Turkevich, G. Kim, *Science*, 169 (1970) 873. When the reduction of palladium metal compound is performed without the use of a coordinating agent, in particular urea, the smallest possible crystallite size that is achieved after optimization of the reaction parameters is 5 nm, as described in WO-A-2009/096783.

Surprisingly it has been found that the use of a coordinating agent according to the process of the present invention leads to a precious metal (nano)crystallite size with a higher dispersion.

The reduction process step is preferably carried out at a pH of between about 2 and 11. More preferably the reduction step is carried out at a pH of between 3.5 and 5.5 when reducing a palladium metal compound; or, at a pH of between 8.5 and 10.5 when reducing a gold metal compound. The deposition step is preferably carried out at a pH value of between 4 to 9. If necessary, the pH can be adjusted by the addition of a base e.g. an alkali metal carbonate (such as $Na_2CO_3$) or an alkali metal hydroxide (such as NaOH).

The catalyst of the present invention may be recovered by suitable separation means, such as, filtration and/or centrifugation. Typically the separated catalyst is then washed with water. The removal of any halides present, such as chloride ions, can be monitored during the washing step by an indicator test using a AgNO$_3$ solution.

In a further embodiment, the precious metal catalyst according to the present invention may be used generally for all chemical reactions for which precious metal catalysts are suitable. Such reactions may include isomerization, oxidation, hydrogenolysis (e.g. hydro-desulfurization), hydrogenation/dehydrogenation and hydro-dewaxing reactions.

These reactions may conveniently be carried out in slurry phase or in a fixed bed in an organic solvent and optionally in the presence of hydrogen, in particular when carrying out hydrogenation reactions either in a three phase system or in a two phase system, where the hydrogen is dissolved in the organic solvent. Preferred conditions for a slurry phase reaction for hydrogenating 3-hexyn-1-ol is a temperature above about 30° C. and a pressure of 1-5 bars H$_2$ (g). Typical conditions which may be used in a slurry phase reaction is a temperature of 20-95° C., and a pressure of 1-10 bars H$_2$ (g).

For the purpose of clarity and a concise description, features are described herein as part of the same or separate embodiments, however, it will be appreciated that the scope of the invention may include embodiments having combinations of all or some of the features described.

The present invention is now elucidated on the basis of some examples, which are not intended to limit the scope of the invention.

EXAMPLES

Example 1: Preparation of a Catalyst Consisting of 2 nm Pd Metal Crystallites Supported on Activated Carbon A 2 L beaker was equipped with baffles and filled with 600 mL water at room temperature (i.e. 20-25° C.). Using a top stirrer, the water was stirred at 300 rpm. The reducing/stabilizing agent (30 mL 30 wt. % Luviquat® Mono CP (hydroxyethyl cetyldimonium phosphate) in water, obtained from Sigma-Aldrich) and the coordinating agent urea (0.30 g) were added in one portion and the mixture was stirred for several minutes. A Pd solution (1.58 g 18.98 wt. % Pd as Na$_2$PdCl$_4$ diluted 60 mL water) was added to the mixture over a period of 30 min, during which the pH of the solution slowly dropped from 5.4 to 4.9. After the addition of the Pd solution the pH of the mixture was set to 5.0 by the addition of NaOH solution (10 wt. % NaOH in water). The mixture was heated to 95° C. (pH of 4.7) and kept at this temperature for two hours, while keeping the water level constant. After cooling, the pH of the colloidal Pd metal suspension was 4.9.

A 2 L beaker was equipped with baffles and filled with 50 g (dry weight) of activated carbon powder and 500 mL water at room temperature (i.e. 20-25° C.) was slowly added to prevent dust formation and to form a slurry. Using a top stirrer, the slurry was stirred at 500 rpm for one hour to obtain a homogeneous suspension. The colloidal Pd metal suspension was added to this suspension over a period of 60 min and the mixture was stirred for an additional hour. The resulting Pd/AC catalyst was filtered off and washed with water until no more Cl was found in the washing water (determined using indicator test using AgNO$_3$ solution). FIG. 1 shows a TEM image of the catalyst according to the present invention obtained and the presence of 2 nm Pd metal crystallites. ICP analysis determined that the catalyst contained 0.48 wt. % Pd.

Figure 2:
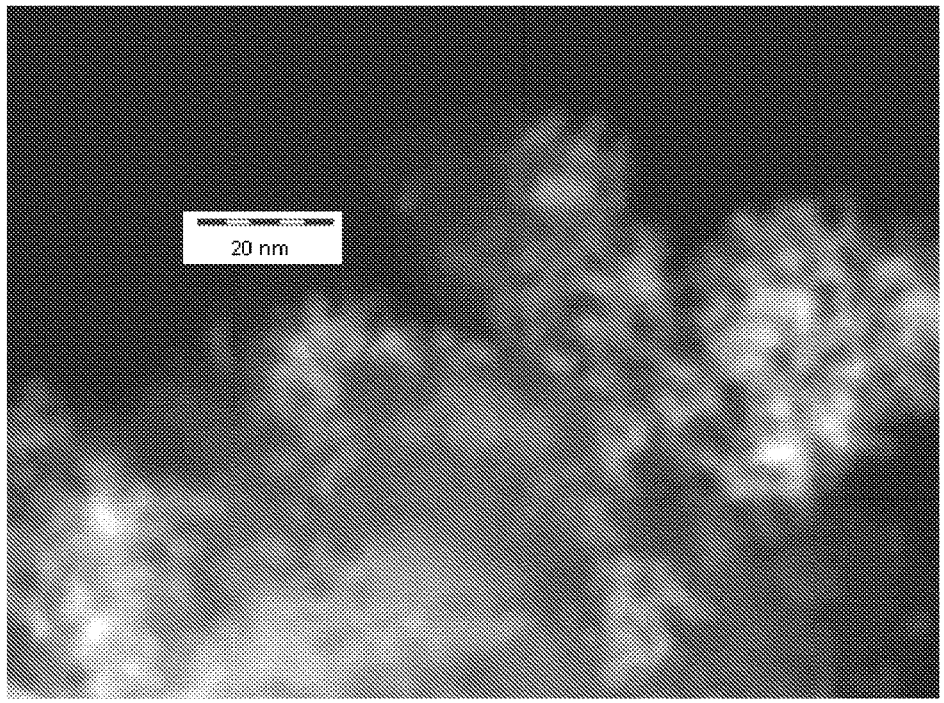

Example 2: Preparation of a Catalyst Consisting of 2 nm Pd Metal Crystallites Supported on Titanium Silicate The reaction of Example 1 was repeated, but the colloidal Pd metal was deposited on 60 g titanium silicate support. FIG. 2 shows a TEM image of the catalyst according to the present invention obtained and the presence of 2 nm Pd metal crystallites. ICP analysis determined that the catalyst contained 0.28 wt. % Pd.

Example 3 (Comparative): Preparation of a Catalyst Consisting of 5 Nm Pd Metal Crystallites Supported on Activated Carbon without Using a Coordinating Agent A 2 L beaker was equipped with baffles and filled with 600 mL water at room temperature (i.e. 20-25° C.). Using a top stirrer, the water was stirred at 300 rpm. The reducing/stabilizing agent (35 mL 30 wt. % Luviquat® Mono CP (hydroxyethyl cetyldimonium phosphate) in water, obtained from Sigma Aldrich) was added in one portion and the mixture was stirred for several minutes. A Pd solution (2.63 g 18.98 wt. % Pd as Na$_2$PdCl$_4$ diluted 100 mL water) was added to the mixture over a period of 30 min, during which the pH of the solution slowly dropped from 5.3 to 5.0. The mixture was heated to 85° C. (pH of 3.2) and the pH was set to 5.0 by the addition of NaOH solution (10 wt. % NaOH in water). The mixture was kept at this temperature for two hours, while keeping the water level constant and re-setting the pH to 5.0 every 30 min. After cooling, the pH of the colloidal Pd metal suspension was 4.9.

Figure 3:
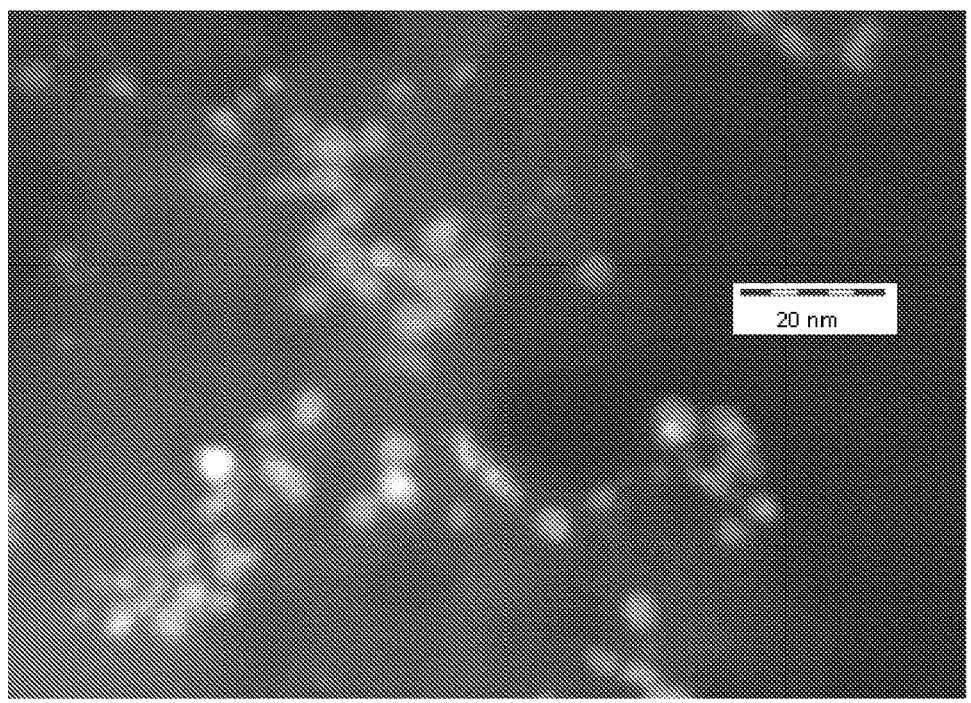

A 2 L beaker was equipped with baffles and filled with 83 g (dry weight) of activated carbon powder and 800 mL water at room temperature (i.e. 20-25° C.) was slowly added to prevent dust formation and to form a slurry. Using a top stirrer, the slurry was stirred at 500 rpm for one hour to obtain a homogeneous suspension. The colloidal Pd metal suspension was added to this suspension over a period of 60 min and the mixture was stirred for an additional hour. The resulting Pd/AC catalyst was filtered off and washed with water until no more Cl was found in the washing water (determined using indicator test using Ag-nitrate solution). FIG. 3 shows a TEM image of the prepared catalyst and the presence of 5 nm Pd metal crystallites. ICP analysis determined that the catalyst contained 0.50 wt. % Pd.

Figure 4:
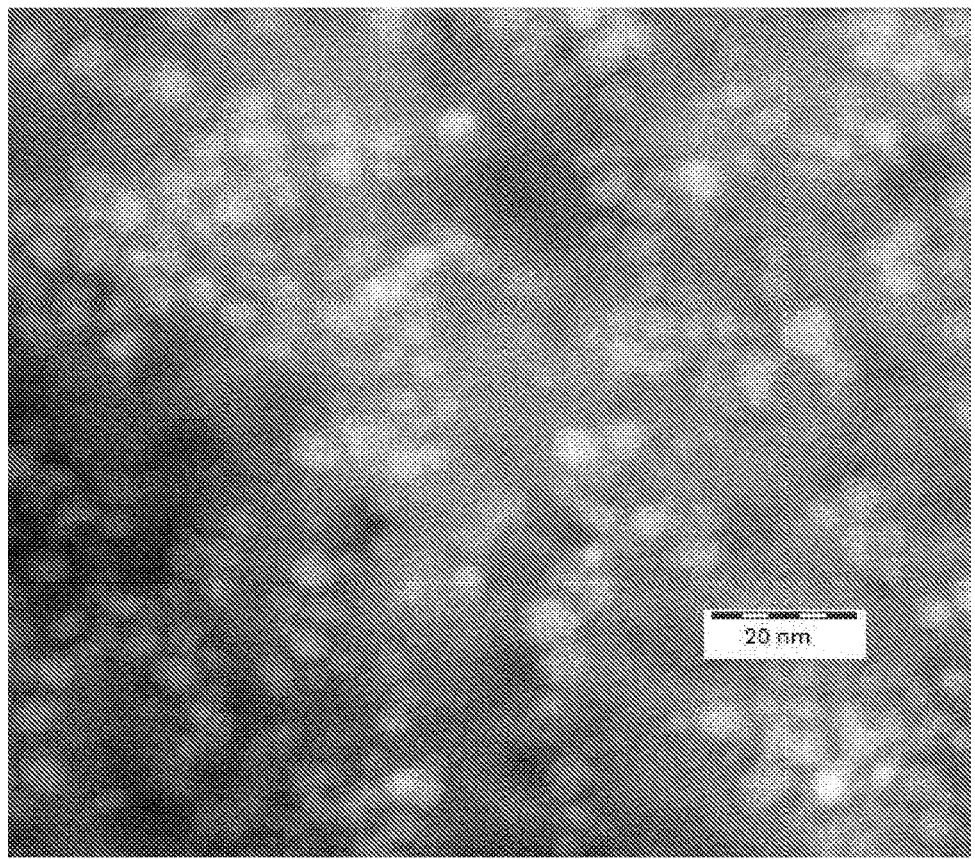

Example 4 (Comparative): Preparation of a Catalyst Consisting of 5 Nm Pd Metal Crystallites Supported on Titanium Silicate without Using a Coordinating Agent The reaction of Example 3 was repeated, but the colloidal Pd metal was deposited on 100 g titanium silicate support. FIG. 4 shows a TEM image of the prepared catalyst and the presence of 5 nm Pd metal crystallites. ICP analysis determined that the catalyst contained 0.29 wt. % Pd.

Example 5: Preparation of a Catalyst Consisting of 10 nm Au Metal Crystallites Supported on Titanium Silicate A 600 mL beaker was equipped with baffles and filled with 200 mL water at room temperature (i.e. 20-25° C.). The reducing/stabilizing agent (7 mL 30 wt. % Luviquat® Mono CP (hydroxyethyl cetyldimonium phosphate) in water, obtained from Sigma-Aldrich) and the coordinating agent urea (0.10 g) were added in one portion and the mixture was stirred for several minutes. An Au solution (0.50 g 20.13 wt. % Au as $AuCl_3$ diluted with 5 mL water) was added to the mixture over a period of 2 min. The pH of the mixture was adjusted to 10 by the addition of NaOH solution (10 wt. % NaOH in water) and kept between 9.5 and 10 for 60 min. The mixture was heated to 50° C. and the pH was kept at value between 9.5 and 10 for another 30 min. The mixture was heated to 85° C. and the pH was kept at a value between 9.5 and 10 for another 120 min, while keeping the water level constant. After cooling, the pH of the colloidal Au metal suspension was about 10.

Figure 5:
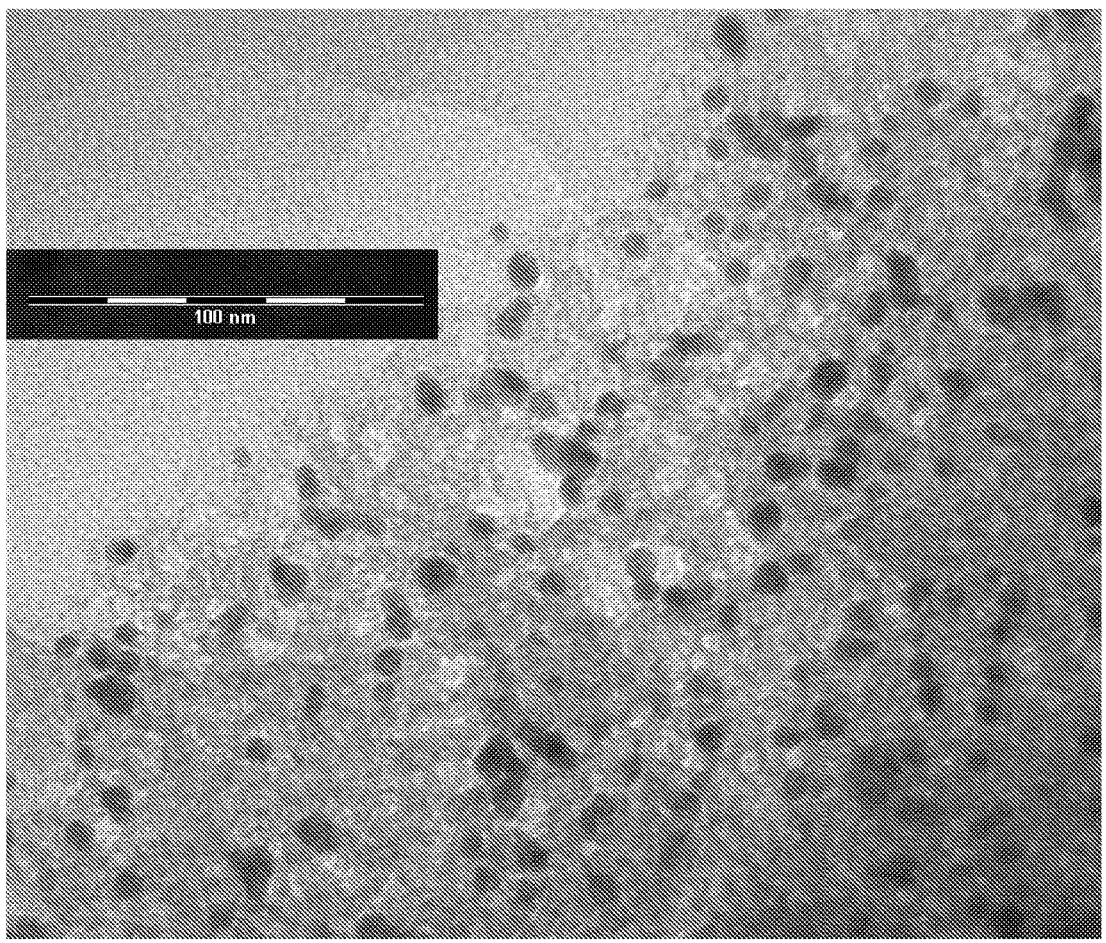

A 600 mL beaker was equipped with baffles and filled with 20 g of titanium silicate powder and 200 mL water at room temperature (i.e. 20-25° C.) was slowly added to prevent dust formation and to form a slurry. Using a top stirrer, the slurry was stirred for 30 min to obtain a homogeneous suspension. The colloidal Au metal suspension was added to this suspension over a period of 90 min and the mixture was stirred for an additional 30 min. The resulting Au/TiS catalyst was filtered off and washed with water until no more Cl was found in the washing water (determined using indicator test using Ag-nitrate solution). FIG. 5 shows a TEM image of the Au catalyst according to the present invention and the presence of 10 nm Au crystallites.

Figure 6:
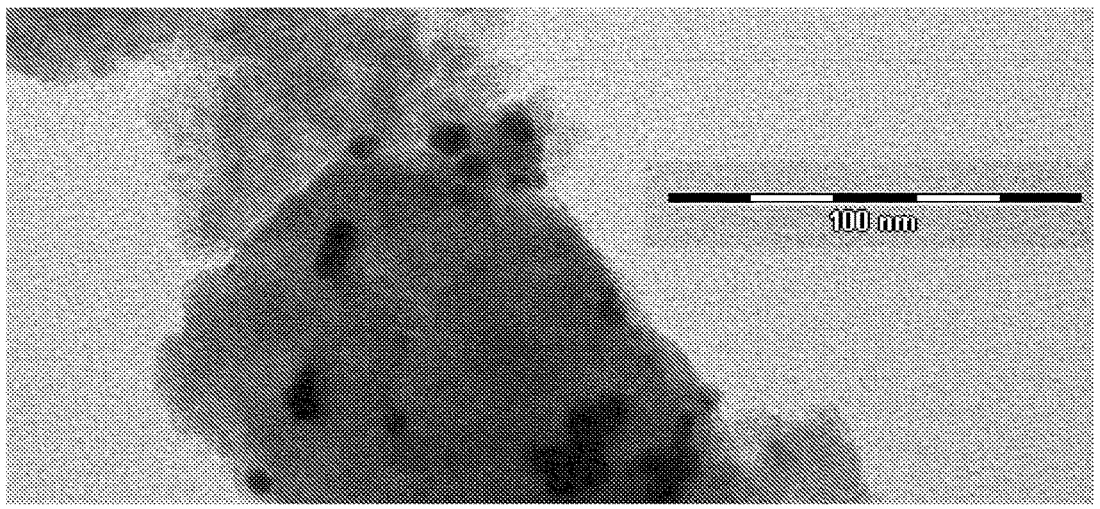

Example 6 (Comparative): Preparation of a Catalyst Consisting of 20 nm Au Metal Crystallites Supported on Titanium Silicate, without the Use of a Coordinating Agent An experiment was carried out similarly to example 5, but without the use of urea. The reduction of Au was complete already at 50° C. and no further heating was required. FIG. 6 shows a TEM image of the prepared catalyst and the presence of 20 nm Au crystallites.

Example 7: Analyses of Catalysts

The following properties of catalysts according to the present invention (Examples 1 and 2) were determined and are shown in Table 1.

The ICP measurement was obtained as described hereinabove.

The PM crystallite sizes mentioned above for the Examples 1-6, of which the PM crystallite sizes of Examples 1-4 are shown in Table 1 below, were measured using TEM. Samples of the catalysts were prepared by first dispersing each of the catalyst in ethanol and applying the resulting dispersions between objective slides which produced a thin film. An ultra-thin carbon TEM carrier was then contacted with each of the thin films.

The prepared samples of the catalysts were investigated using a Tecnai G2-F20ST machine (FEI Company, Hillsboro, USA) operated at 200 keV. Energy Dispersive X-ray spectroscopy (EDXS) was applied to determine chemical compositions at distinct locations of the sample using an EDXi-detection system with an energy resolution of 131 eV at Mn— Kα (EDAX, Mahwah, USA). Images and spectroscopy data were evaluated using the OlympusiTEM 5.2 (Build 3554) (Olympus, Tokyo, Japan) and FEI TIA 4.1.202 (FEI Company, Hillsboro, USA) software packages. For PM crystallite size determination the microscopes magnification was calibrated using a MAG*I*CAL calibration sample (Technoorg Linda Ltd., Budapest, Hungary). The average PM crystallite size was determined by manually measuring the smallest diameter of about 200 PM crystallites per sample using the Olympus iTEM 5.2 software.

The XPS measurements were carried out on the catalyst samples as described hereinabove.

The surface enrichment value (SEV) was determined using the above-mentioned formula (I).

The same analyses were also carried out for the comparative catalysts of Examples 3 and 4 and are shown in Table 1 below.

The following commercially available catalysts of Escat™ 1421 (Pd 5 wt. % on AC, reduced, from STREM Chemicals, Inc.), Escat™ 1621 (Pd 5 wt. % on AC, reduced, from STREM Chemicals, Inc.), Escat™ 1911 (Pd 3 wt. % on AC, reduced, from STREM Chemicals, Inc.), Escat™ 1941 (Pd 5 wt. % on AC, reduced, from STREM Chemicals, Inc.) and Escat™ 1971(Pd 5 wt. % on AC, reduced, from STREM Chemicals, Inc.) were similarly analyzed, with the exception that the Pd crystallite size was measured using CO chemisorption. The results of these analyses are also shown in Table 1 below.

The CO chemisorption measurements of the above-mentioned commercially available catalysts were made using an Autochem II 2920 Chemisorption Analyzer from Micromeritics Instrument Corporation. The catalyst samples were prepared by drying the catalysts at 105° C. overnight o remove adsorbed water and other volatiles. The dried catalysts were loaded in amounts of about 0.1 to 0.2 g each into a sample tube. The catalyst samples were then pretreated with $H_2$ in Ar: 15 vol. % gas flow (50 mL/min) and a temperature ramp rate of 10° C./min to 200° C., and was held at a temperature of 200° C. for 30 min. The catalyst samples were then cooled under He gas flow (50 mL/min) to 50° C. A CO pulse (loop volume 0.39 mL STP) was injected into the He gas flow (50 mL/min) for 6 times with an interval of 5 min). Lastly, the catalyst samples were flushed with a He gas flow (50 mL/min) for 3 min. The effective metallic surface area per gram of PM and the average size of the PM nanocrystallites were determined using the data measured from the catalyst samples and the integrated software package of the Autochem II 2920 Chemisorption Analyzer.

TABLE 1

| Catalyst | Support (S) | ICP (wt. %) | Pd crystallite size (nm) | XPS (wt. %) | SEV |
| --- | --- | --- | --- | --- | --- |
| Example 1 | AC | 0.48 | 2* | 5.6 | 10.7 |
| Example 2 | TiS | 0.28 | 2* | 22.4 | 79 |
| Example 3 | AC | 0.50 | 5* | 5.0 | 9.0 |
| Example 4 | TiS | 0.29 | 5* | 24.3 | 83 |
| Escat ™ 1421 | AC | 5 | 4.3# | 14.4 | 1.9 |
| Escat ™ 1621 | AC | 5 | 4.0# | 17.8 | 2.6 |
| Escat ™ 1911 | AC | 3 | 3.0# | 21.0 | 6.0 |
| Escat ™ 1941 | AC | 5 | 5.2# | 24.1 | 3.8 |
| Escat ™ 1971 | AC | 5 | 4.3# | 17.3 | 2.5 |

*as determined by TEM
as determined by CO chemisorption

As can be seen from the above results, the catalysts according to the present invention (Examples 1 and 2) have both a smaller Pd crystallite size and a higher SEV value than any of the comparative catalysts analyzed.

Example 8: Semi-Hydrogenation of 3-Hexyn-1-Ol Using a Supported Palladium Catalyst A 250 mL stainless steel autoclave was charged separately with an amount of the catalysts of Examples 1-4 resulting in 1.25 mg Pd in the reactor and 100 g of a 4.5 wt. % solution of 3-hexyn-1-ol in 96 wt. % ethanol was added to the reactor. The autoclave was closed and the mixture was heated to 30° C. with stirring. The stirring was stopped, and the air was replaced by flushing hydrogen over the mixture. After flushing the autoclave was pressurized with 3 bars of hydrogen. The stirring was resumed (1500 rpm) and the hydrogen consumption was recorded. After 90 min the stirring was stopped. The reaction rates r1 (semi-hydrogenation) and r2 (over-hydrogenation) are calculated in mL $H_2$ per min from the $H_2$ uptake curve.

Figure 7:
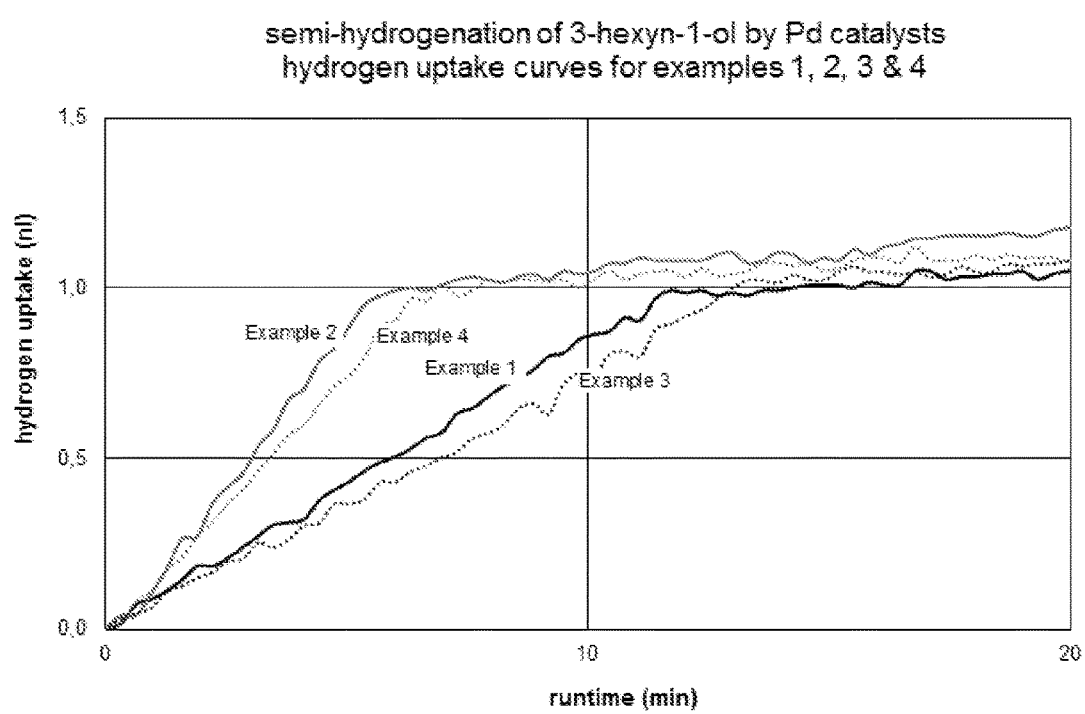
FIG. 7 shows the hydrogen uptake (nL) versus the runtime (min) when using the catalysts of Examples 1-4 in the semi-hydrogenation of 3-hexyn-1-ol.

FIG. 7 shows the hydrogen uptake (nL) versus the runtime (min) using the catalysts of Example 1-4 in the semi-hydrogenation of 3-hexyn-1-ol. Table 2 shows the r1 and r2 values (in $H_2$ per min) as determined from the hydrogen uptake. This shows that the catalysts according to the present invention (Example 1 on activated carbon and Example 2 on titanium silicate) are more than 10% more active in the desired semi-hydrogenation than the comparative examples (Examples 3 and 4, respectively).

TABLE 2

| Catalyst | r1 ($H_2$ per min) | r2 ($H_2$ per min) |
|---|---|---|
| Example 1 | 85 | 7.4 |
| Example 2 | 189 | 7.5 |
| Example 3 | 75 | 7.5 |
| Example 4 | 156 | 4.6 |

The invention claimed is:

1. A precious metal catalyst, comprising nanocrystallites of at least one precious metal on a powder support, wherein:
the precious metal is palladium metal, gold metal, or a combination thereof;
when the precious metal comprises the palladium metal, the precious metal catalyst comprises a palladium metal catalyst comprising nanocrystallites of palladium metal having an average size of from 1 to less than 5 nm, and the palladium metal catalyst has a surface enrichment value of from at least 6.5 to at most 150;
when the precious metal comprises the gold metal, the precious metal catalyst comprises a gold metal catalyst comprising nanocrystallites of gold metal having an average size of from 3 to less than 15 nm, and the gold metal catalyst has a surface enrichment value of from at least 3 to at most 150;
the surface enrichment value (SEV) is determined from the following formula (I):

SEV=(XPS wt. %–ICP wt. %)/ICP wt. %;  (I)

wherein XPS wt. % is the X-ray photoelectron spectroscopy (XPS) measurement and ICP wt. % is the inductively coupled plasma (ICP) measurement of the precious metal content in weight percent of said catalyst.

2. The catalyst according to claim 1, comprising the precious metal in an amount of between 0.01 and 20 wt. %, based on a weight of the catalyst.

3. The catalyst according to claim 1, wherein:
the palladium metal catalyst has a surface enrichment value of at least 8, and the palladium metal catalyst has a surface enrichment value of at most 120; and
the gold metal catalyst has a surface enrichment factor of at least 5 and, has a surface enrichment value of at most 120.

4. The catalyst according to claim 1, wherein:
the nanocrystallites of the palladium metal have an average size between 1 and 4 nm; and
the nanocrystallites of the gold metal have an average size between 3 and 13.

5. The catalyst according to claim 1, wherein the powder support is selected from the group consisting of silica, alumina, zirconia, titanium oxide, ceria, magnesium oxide, zinc oxide, metal silicates, metal aluminates, zeolites, carbon nanotubes, carbon nanofibres, graphitic carbon and activated carbon and combinations thereof.

6. The catalyst according to claim 1, wherein the average particle size of the powder support is between 0.1 and 500 micron.

7. A process for preparing a precious metal catalyst, the process comprising:
reducing a precious metal compound in an aqueous solution by contacting said solution with a reducing agent, a stabilizing agent and a coordinating agent thereby forming a colloidal precious metal suspension;
contacting the suspension with a powder support; and
recovering the precious metal catalyst.

8. The process according to claim 7, wherein the precious metal is palladium metal, gold metal, or a combination thereof.

9. The process according to claim 7, wherein the reducing agent is selected from the group consisting of a quaternary ammonium salt, sodium formate, formic acid, sodium citrate, citric acid, hydrazine, a $C_1$-$C_4$ alcohol, a diol, a polyol, a borohydride, formaldehyde, hypophosphite, a metal alkalyde hydrogen and combinations thereof.

10. The process according to claim 7, wherein the stabilizing agent is selected from the group consisting of a quaternary ammonium salt, a donor ligand, a polymer, a surfactant and combinations thereof.

11. The process according to claim 7, wherein the coordinating agent is urea, ammonia, or both.

12. The process according to claim 7, wherein the support is selected from the group consisting of silica, alumina, zirconia, titanium oxide, ceria, magnesium oxide, zinc oxide, a metal silicate, a metal aluminate, a zeolite, a carbon nanotube, a carbon nanofiber, graphitic carbon, activated carbon and combinations thereof.

13. A precious metal catalyst obtained by the process of claim 7.

14. A process, comprising performing a reaction in the presence of the precious metal catalyst of claim 1, wherein the reaction is a hydrogenation/dehydrogenation, isomerization, oxidation, hydrogenolysis or hydro-dewaxing reaction.

15. The catalyst according to claim 1, wherein the nanocrystallites of at least one precious metal are edge-coated on the powder support.

16. The process according to claim 7, wherein the precious metal suspension is edge-coated on the powder support.

17. The precious metal catalyst according to claim 13, wherein the catalyst has an edge-coated metal distribution on the powder support.

18. The process according to claim 7, wherein the coordinating agent is urea.

* * * * *

UNITED STATES PATENT AND TRADEMARK OFFICE
CERTIFICATE OF CORRECTION

PATENT NO. : 10,232,354 B2
APPLICATION NO. : 15/559837
DATED : March 19, 2019
INVENTOR(S) : Witte et al.

Page 1 of 1

It is certified that error appears in the above-identified patent and that said Letters Patent is hereby corrected as shown below:

In the Specification

Column 1, Lines 8-9, "This application is a National Stage of PCT/IB2016/051446, which was filed on Mar. 18, 2016. This application", should read -- This application is a National Stage of PCT/IB2016/051546, which was filed on Mar. 18, 2016. This application --

Column 1, Lines 66-67, "nanop articles", should read -- nanoparticles --

Signed and Sealed this
Twenty-first Day of April, 2020

Andrei Iancu
*Director of the United States Patent and Trademark Office*